United States Patent [19]

Fazio et al.

[11] Patent Number: 5,006,643

[45] Date of Patent: Apr. 9, 1991

[54] PROCESS FOR PREPARING ISOTHIOCYANATO FUNCTIONALIZED METAL COMPLEXES

[75] Inventors: Michael J. Fazio; Douglas K. Pollock; Nicolas J. Kotite, all of Midland, Mich.

[73] Assignee: The Dow Chemical Company, Midland, Mich.

[21] Appl. No.: 383,103

[22] Filed: Jul. 20, 1989

Related U.S. Application Data

[63] Continuation-in-part of Ser. No. 65,739, Jun. 24, 1987, and a continuation-in-part of Ser. No. 211,496, Jun. 24, 1988, abandoned, and a continuation-in-part of Ser. No. 265,158, Oct. 31, 1988, abandoned, and a continuation-in-part of Ser. No. 370,956, Jun. 21, 1989, and a continuation-in-part of Ser. No. 289,172, Dec. 23, 1988, abandoned.

[51] Int. Cl.$^5$ .................... C07F 15/00; C07C 263/10; A61K 43/00
[52] U.S. Cl. .................... 534/10; 534/11; 534/14; 534/15; 424/1.1; 424/85.91; 556/136; 556/137; 560/347
[58] Field of Search .................... 560/347; 424/1.1; 534/10, 14, 15; 556/136, 137

[56] References Cited

U.S. PATENT DOCUMENTS

4,454,106  6/1984  Gansow et al. ............... 424/1.1
4,885,363  12/1989  Tweedle et al. ............... 534/15 X

FOREIGN PATENT DOCUMENTS

0139675  1/1987  European Pat. Off. .
0296522  12/1988  European Pat. Off. .

OTHER PUBLICATIONS

March, J. *Advanced Organic Chemistry*, 3d ed., (John Wiley and Sons, New York) 1985.
Forsberg et al., *Inorg. Chem.* v. 8, pp. 883–888 (1969).
Morrison and Boyd, *Organic Chemistry*, 2d ed., Allyn and Bacon, Inc., Boston; pp. 751, 758, 759 (1969).
Degering, ed. *Organic Chemistry*, 6th ed., Barnes & Noble, Inc., New York, p. 144, (1962).
Gansow et al., *Inorg. Chem.* 25, 2772–2781 (1986).
Meares et al., *Analytical Biochem.* 142, 68–78 (1984).

*Primary Examiner*—Richard D. Lovering
*Assistant Examiner*—John M. Covert
*Attorney, Agent, or Firm*—Karen L. Kimble

[57] ABSTRACT

The present invention is directed to a novel process for preparing isothiocyanate functionalized chelates by reacting amino functionalized chelates with thiophosgene.

14 Claims, No Drawings

PROCESS FOR PREPARING ISOTHIOCYANATO FUNCTIONALIZED METAL COMPLEXES

CROSS REFRENCES TO RELATED APPLICATIONS

This application is a continuation-in-part of our co-pending application Ser. No. 065,739 filed June 24, 1987, of application Ser. No. 211,496 filed June 24, 1988, now abandoned, of application Ser. No. 265,158 filed Oct. 31, 1988, now abandoned, of our co-pending application Ser. No. 370,956, filed June 21, 1989 and of application Ser. No. 289,172, filed Dec. 23, 1988, now abandoned.

BACKGROUND OF THE INVENTION

Functionalized chelants, or bifunctional coordinators, are known to be capable of being covalently attached to an antibody having specificity for cancer or tumor cell epitopes or antigens. Radionuclides complexes of such antibody/chelant conjugates are useful in diagnostic and/or therapeutic applications as a means of conveying the radionuclide to a cancer or tumor cell. See, for example, Meares et al., *Anal. Biochem.* 142, 68–78 (1984); and Krejcarek et al., *Biochem. and Biophys. Res. Comm.* 77, 581–585 (1977).

The present invention relates to a process for preparing isothiocyanto fuctionalized metal complexes. A radionuclide can be used in these complexes.

Isothiocyanto functionalized ligands are reported in the literature and are being used to conjugate radioactive isotopes to antibodies. For example see Gansow et al., *Inorg. Chem.* 25, 2772-81 (1986); Meares et al., *Analytical Biochem.* 142, 68-78 (1984); U.S. Pat. No. 4,454,106.

The methodology taught in the art to prepare such complexes involves treatment of an antibody/chelant conjugate with the radionuclide to form a complex followed by purification of the complex. A major disadvantage of such methodology is that the radionuclide (a lanthanide or transition metal) must be kinetically labile in order to be rapidly sequestered by the antibody/chelant conjugate.

Another disadvantage associated with the use of labile radionuclides for antibody labelling is that substitutionally labile trace metals (which are not radioactive) are frequently incorporated into the chelate. Competition for such non-active trace metals diminishes the biological efficacy of the antibody/chelate complex since a lower quantity of radionuclide is delivered to the target site.

Mikoler et al., European published application No. 139,675, teach the preparation of isothiocyanate fuctionalized chelates which can subsequently be conjugated to bio-organic molecules, e.g. haptens, antigens, antibodies. These complexes are prepared by chelating the isothiocyanate functionalized ligand.

SUMMARY OF THE INVENTION

The present invention is directed to a novel process to prepare isothiocyanate fuctionalized chelates by thiophosgenation of amino fuctionalized chelates.

DETAILED DESCRIPTION OF THE INVENTION

The present process concerns the preparation of the isothiocyanto function on a ligand after the metal has been chelated with the ligand. The formation of the isothiocyanto moiety on the ligand after the complex has been formed is important for several reasons. One advantage is when the complex requires heating or severe extremes in pH to form the complex, such as with rhodium or lanthanide macrocycles, the present process avoids the destruction of the isothiocyanate fuctionality during chelation. A second advantage is when there are other primary or secondary amines present in the ligand, formation of the isothiocyanate fuctionalized ligand prior to chelation is impractical due to side reactions. A third advantage is that by forming the complex at as early a stage in the reaction as possible complexation of undesired metals is reduced and thus purity of the final product is enhanced. Another advantage is that by forming the complex prior to the introduction of the isothiocyanate, purification of the complex, such as by ion exchange chromatography, is simplified. The added complication of the hydrolysis of the isothiocyanate during purification is also reduced.

The present process provides a method to prepare isothiocyanates by thiophosgenation of amino fuctionalized chelates which results in a process that is rapid with high yield and provides a product having low metal contamination present. As there are a fewer number of reactions required overall by the present process on the ligand prior to chelation, the amount of undesired metal contamination is reduced.

The ligands of interest are generally strong chelators for many different metals which may be present in the reagents or containers used to store or transfer the ligand. Although amino fuctionalized chelates of many types can be used, the chelates formed from ligands that are aminocarboxylic acid chelants, aminophosphonic acid chelants or polyaza chelants are particularly preferred.

One of the possible classes of ligands useful in this process are aminocarboxylic acid chelants. Examples of some of the possible aminocarboxylic acid chelants are given in Table I following and which are named as follows:

I A is p-aminobenzyl ethylenediaminetetraacetic acid, the preparation of which is given in U.S. Pat. No. 4,622,420 and *J. Med. Chem.* 17(4), 1304 (1974);

I B is p-aminobenzyl hydroxyethylethylenediaminetriacetic acid, the preparation of which is given in U.S. Pat. No. 4,622,420;

I C is p-aminobenzyl diethylenetriaminepentaacetic acid, the preparation of which is given in U.S. Pat. Nos. 4,622,420 and 4,647,447;

I D is N'-p-aminobenzyl diethylenetriamine-N,N,N'',N''-tetraacetic acid, the preparation of which is given in *J. Radioanalytical Chem.* 57(12), 553 (1980);

I E is 6-(p-aminobenzyl)-1,4,8,11-tetraazacyclotetradecane-1,4,8,11-tetraacetic acid, the preparation of which is given in *Analytical Biochem.* 148, 249–253 (1985);

I F is α-(4-aminobenzyl)-1,4,7,10-tetraazacyclododecane-1,4,7,10-tetraacetic acid, the preparation of which is given in our U.S. application Ser. No. 211,496 by S. Baughman et al., now abandoned, the disclosure of which is hereby incorporated by reference;

I G is α-(4-aminobenzyl)-1,4,7,10-tetraazacyclododecane-1,4,7-triacetic acid, the preparation of which is given in our U.S. application Ser. No. 211,496 by S. Baughman et al., now abandoned, the disclosure of which is hereby incorporated by reference;

I H is 1-[2-(4-aminophenyl)ethyl]-1,4,7,10-tetraazacyclododecane-4,7,10-triacetic acid, the preparation of which is given in our U.S. application Ser. No. 211,496 by S. Baughman et al., now abandoned, the disclosure of which is hereby incorporated by reference;

I I is α-[2-(4-aminophenyl)ethyl]-1,4,7,10-tetraazacyclododecane-1,4,7,10-tetraacetic acid, the preparation of which is given in our U.S. application Ser. No. 211,496 by S. Baughman et al., now abandoned, the disclosure of which is hereby incorporated by reference;

I J is 1-(5-amino-2-methoxybenzyl)-1,4,7,10-tetraazacyclododecane-4,7,10-triacetic acid, the preparation of which is given in our U.S. application Ser. No. 211,496 by S. Baughman et al., now abandoned, the disclosure of which is hereby incorporated by reference;

I K is 1-(5-amino-2-hydroxybenzyl)-1,4,7,10-tetraazacyclododecane-4,7,10-triacetic acid, the preparation of which is given in our U.S. application Ser. No. 211,496 by S. Baughman et al., now abandoned, the disclosure of which is hereby incorporated by reference;

I L is 2-[(2-{[bis(carboxymethyl)]amino}ethyl)-(carboxymethyl)amino]-2-[5-amino-2-(carboxymethyloxy)-phenyl]ethanoic acid, the preparation of which is given in our U.S. application Ser. No. 265,158 by D. Wilson et al., now abandoned, the disclosure of which is hereby incorporated by reference;

I M is 2-[(2-{[bis(carboxymethyl)]amino}ethyl)-(carboxymethyl)amino]-2-(5-amino-2-hydroxyphenyl)-ethanoic acid the preparation of which is given in our U.S. application Ser. No. 265,158 by D. Wilson et al., now abandoned, the disclosure of which is hereby incorporated by reference;

I N is 2,6-bis{[(2-{[bis(carboxymethyl)]amino}-ethyl)(carboxymethyl)]aminomethyl}-4-(amino)phenol the preparation of which is given in our U.S. application Ser. No. 265,158 by D. Wilson et al., now abandoned, the disclosure of which is hereby incorporated by reference.

I O is α-(4-aminophenyl)-1,4,7,10-tetraazacyclododecane-1,4,7,10-tetraacetic acid, the preparation of which is given in our U.S. application Ser. No. 211,496 by S. Baughman et al., now abandoned, the disclosure of which is hereby incorporated by reference;

I P is α-(4-aminophenyl)-1,4,7,10-tetraazacyclododecane-1,4,7-triacetic acid, the preparation of which is given in our U.S. application Ser. No. 211,496 by S. Baughman et al., now abandoned, the disclosure of which is hereby incorporated by reference; and I Q is α-[2-(4-aminophenyl)ethyl]-1,4,7,10-tetraazacyclododecane-1-(R,S)-acetic-4,7,10-tris-(R-methylacetic) acid, the preparation of which is given in our copending U.S. application Ser. No. 370,956 by Roberta Cheng et al., the disclosure of which is hereby incorporated by reference.

TABLE I

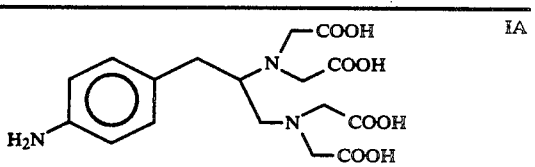

IA

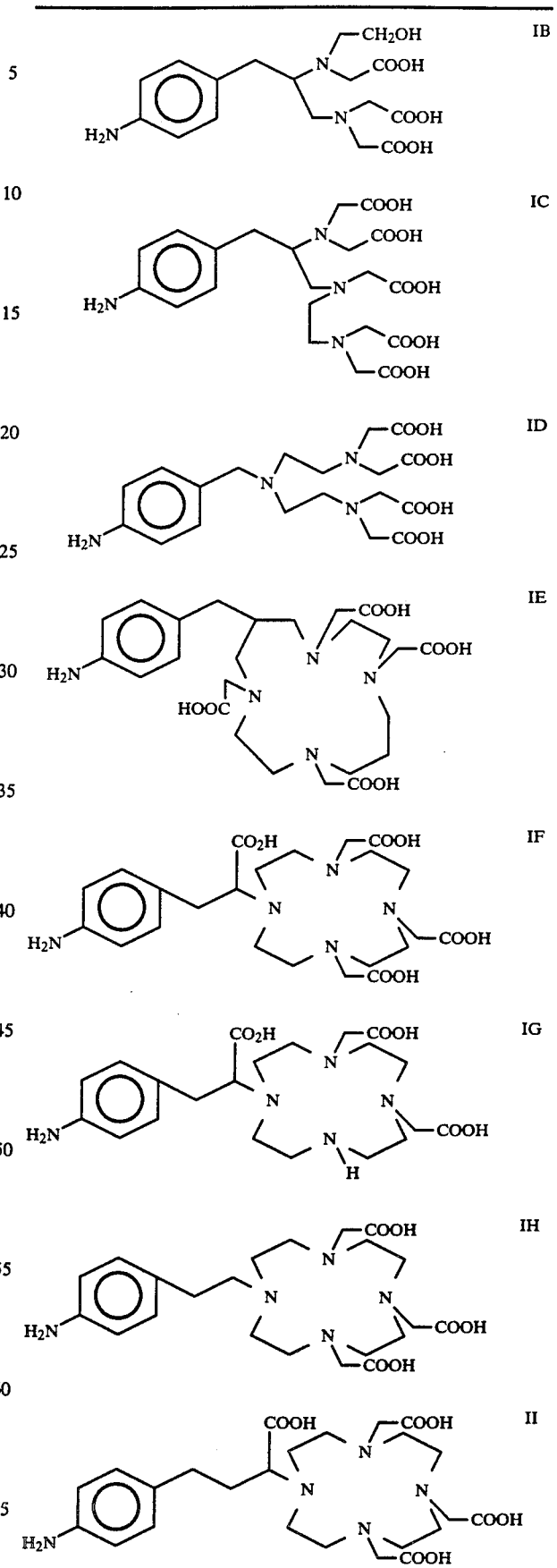

TABLE I-continued

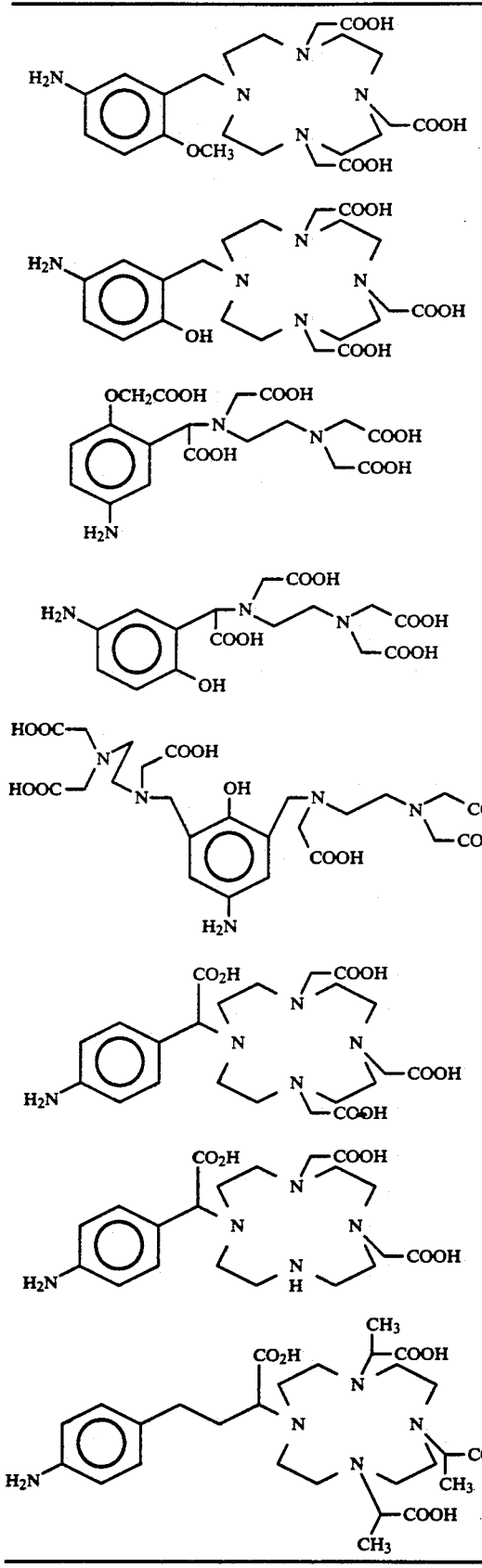

Another one of the possible classes of ligands useful in this process are aminophosphonic acid chelants. Examples of some of the possible aminophosphonic acid chelants are given in Table II following and which are named as follows:

II A is p-aminobenzyl ethylenediaminetetramethylenephosphonic acid, the preparation of which is given below;

II B is 6-(p-aminobenzyl)-1,4,8,11-tetraazacyclotetradecane-1,4,8,11-tetramethylenephosphonic acid, the preparation of which is given below; and II C is 1-[2-(4-aminophenyl)ethyl]-1,4,7,10-tetraazacyclododecane-4,7,10-trimethylenephosphonic acid, the preparation of which is given below.

Aminophosphonic acids can be prepared by a number of known synthetic techniques. Of particular importance is the reaction of a compound containing at least one reactive amine hydrogen with a carbonyl compound (aldehyde or ketone) and phosphorous acid or derivative thereof. [See the procedure of Moeoritzer and Irani, J. Org. Chem. 31, 1603 (1966).] For example, p-nitrobenzyl ethylenediamine reacted with formaldehyde and phosphorous acid can be converted to the p-nitrobenzyl ethylenediaminetetramethylenephosphonic acid. Reduction of the nitro group would yield p-aminobenzyl ethylenediaminetetramethylenephosphonic acid.

TABLE II

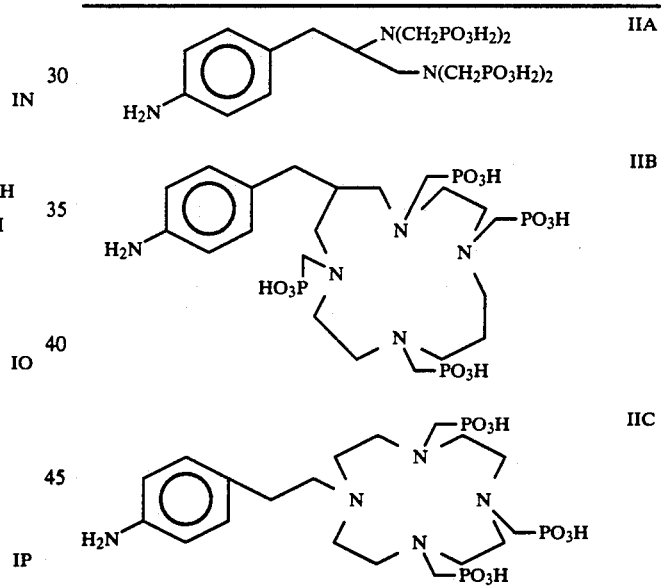

A futher suitable class of ligands which may be used in the process of this invention are polyaza chelants. Examples of some of these polyaza chelants are given in Table III and are named as follows:

III A is 3-[(4-aminophenyl)methyl]-1,5,8,12-tetraazacyclotetradecane, the preparation of which is given in our copending U.S. application Ser. No. 065,739 by W. J. Kruper et al., the disclosure of which is hereby incorporated by reference;

III B is 6-[(4-aminophenyl)methyl]-1,4,8,11-tetraazaundecane, the preparation of which is given in our copending U.S. application Ser. No. 065,739 by W. J. Kruper et al., the disclosure of which is hereby incorporated by reference;

III C is 1,4,7,10-tetraaza-1-[(4-aminophenyl)methyl]-cyclododecane, the preparation of which is given in our copending U.S. application Ser. No. 065,739 by W. J.

Kruper et al., the disclosure of which is hereby incorporated by reference; and

IV D is 6-(3-aminopropyl)-1,4,7,11-tetraazaundecane, the preparation of which is given in our copending U.S. application Ser. No. 065,739 by W. J. Kruper et al., the disclosure of which is hereby incorporated by reference.

TABLE III

IIIA

IIIB

IIIC

IIID

The thiophosgene is added in excess to the mixture. The amount of excess used depends on the concentration of the starting amino fuctionalized chelate. The lower the concentration of chelate, the larger the excess of thiophosgene, to insure the rapid and complete conversion of amine to the isothiocyanate. For example, if the concentration of chelate is $10^{-3}M$, the ratio of thiophosgene to chelate is 5–20:1; if the concentration of chelate is $10^{-8}M$, the ratio of thiophosgene to chelate is several thousand times higher (i.e. $10^5$:1). The excess thiophosgene is removed by conventional techniques such as evaporation, chromatrography, or extraction.

The process is run in a polar solvent, especially water or polar organic solvents in which the complexes are soluble. Mixtures of solvents such as water and a non-reactive solvent are especially preferred, such as, for example, water/acetonitrile, water/dimethylformamide, water/chloroform, water/methylene chloride, water/ethanol, and water/butanol. Then solvent can be a single phase or two phase system, but it is desirable that the complex be in solution.

The pH of the reaction may be from 2–10, preferrably from 6–8. The pH stability of the complex may restrict the operable pH range. Some complexes, such as ethylenediaminetetraacetic acid chelates of lanthanides, are not very stable at pH 2. Additional base can be used to maintain the pH in the desired range or conventional buffers can be used.

The time of reaction when carried out with excess thiophosgene is very fast and usually complete after 5–10 minutes at room temperature (about 15 to about 25° C.). Higher or lower temperatures can be used (e.g. about 0 to about 50° C.) but room temperature is preferred. Ambient pressure is used although higher or lower pressures can be employed. Pressure is not a critical feature of the present process.

The yield for the process is at least 50% by weight.

Although any metal, whether a radioactive metal or not, can be used which complexes with the amino functionalized chelant. The complexes formed should have reasonable stability such that the metal complex is not readily dissociated. Complexes with stability constants of $10^5$ should be suitable. The radionuclides are prefered because of the use of the resulting products in a pharmaceutical drug for therapy and/or diagnosis. Especially preferred radioactive isotopes are those of samarium (Sm-153), holmium (Ho-166), ytterbium (Yb-175), lutetium (Lu-177), gadolinium (Gd-159), yttrium (Y-90), rhodium (Rh-105), indium (In-111), and technecium (Tc-99 m).

PREPARATION OF STARTING MATERIALS

Some of the chemicals used were obtained commercially from various sources such as thiophosgene was from Aldrich Chemicals.

The preparation of many of the starting materials for this process can be found in the literature. 1-(4-aminobenzyl) diethylenetriaminepentaacetic acid was prepared according to the procedure of M. W. Brechbiel, et al., Inorg. Chem., 25, 2772–2781 (1986).

The preparation of α-(4-aminobenzyl)-1,4,7,10-tetraazacyclododecane-1,4,7,10-tetraacetic acid, samarium(III) complex, α-(4-aminobenzyl)-1,4,7,10-tetraazacyclododecane-1,4,7,10-tetraacetic acid, yttrium complex, and 1-[2-(4-aminophenyl)ethyl]-1,4,7,10-tetraazacyclododecane-4,7,10-triacetic acid are shown in our copending U.S. application Ser. No. 211,496 by S. Baughman et al., now abandoned, the disclosure of which is hereby incorporated by reference.

Radionuclides can be produced in several ways. In a nuclear reactor a nuclide is bombarded with neutrons to obtain a radionuclide, e.g.

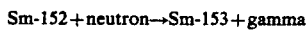

Sm-152+neutron→Sm-153+gamma

Another method of obtaining radionuclides is to bombard nuclides with particles produced by a linear accelerator or a cyclotron. Yet another way is to isolate the radionuclide from a mixture of fission products. The method of obtaining the nuclides employed in the present invention is not critical thereto.

The present process has been used to make valuable synthetic precursors for radioactive pharmaceuticals. [See our U.S. application Ser. No. 211,496 by S. Baughman et al., now abandoned, the disclosure of which is hereby incorporated by reference, our U.S. application Ser. No. 265,158 by D. Wilson et al., now abandoned, the disclosure of which is hereby incorporated by reference, and our copending U.S. application Ser. No. 65,739 by W. J. Kruper et al., the disclosure of which is hereby incorporated by reference.]

In the following examples, the following terms and conditions were used unless otherwise specified.

GLOSSARY

BA-2,3,2-tet means 6-[(4-aminophenyl)methyl]-1,4,8,11-tetraazaundecane;

BITC-2,3,2-tet means 6-[(4-isothiocyanatophenyl)methyl]-1,4,8,11-tetraazaundecane;

HEPES means N-2-hydroxyethylpiperazine-N'-2-ethane sulfonic acid; and

TLC means thin layer chromotography.

GENERAL EXPERIMENTAL

Mass spectra were obtained on a VG ZAB-MS high resolution mass spectrometer (fast atom bombardment with xenon, using 3:1 dithiothreitol:dithioerythritol).

$R_f$ values are reported using these solvent systems and commercially available, normal phase, silica TLC plates (GHLF 250 micron, Analtek Inc.).

The following HPLC system was used for analyses and sample separations:

System I consisted of LKB 2150 pump, and 2152 controller, a UV detector-LKB 2238 UV Cord, a Berthold LB 506 A HPLC Radioactivity Monitor (of the International Berthold Group) and a Gilson Fraction collector 201-202 (Gilson International, Middleton, Wis.).

All percentages are by weight unless stated otherwise.

Samarium-153 was produced by the Reserarch Reactor, University of Missouri (Columbia, MO.). It was supplied as a solution of 0.2 to 0.3 millimolar (mmole) concentration of samarium in 0.1N hydrochloric acid (HCl).

The invention will be further clarified by consideration of the following examples, which are intended to be purely exemplary of the use of this invention.

PROCESS OF THE INVENTION

Example 1

Preparation of [$^{105}$Rh(BITC-2,3,2-tet)Cl$_2$]+

[$^{105}$Rh(BA-2,3,2-tet)Cl$_2$]+ was converted to the reactive [$^{105}$Rh(BITC-2,3,2-tet)Cl$_2$]+ derivative by mixing 2 ml of the [$^{105}$Rh(BA-2,3,2-tet)Cl$_2$]+ (approximately 5 mCi/ml, 1×10$^{-4}$M) with 0.002 ml of thiophosgene. The reaction was allowed to proceed 15 minutes at room temperature. The product was isolated by passing solution through a Hamilton PRP-1 Chrompak. The [$^{105}$Rh(BITC-2,3,2-tet)Cl$_2$]+ was eluted with 2 mL of acetonitrile. The product was characterized by comparison to known standards using cation exchange and reverse phase chromatography. Using this procedure yields of between 50 to 85% were obtained.

Example 2

Preparation of [Rh(BITC-2,3,2-tet)Cl$_2$]+

[Rh(BA-2,3,2-tet)Cl$_2$]+ (10 mg) was dissolved in a mixture of 5 ml of pH 7 phosphate buffer (0.3M), 0.5 ml of acetonitrile, and 1 g of sodium chloride. The reaction mixture was stirred at room temperature (about 22° C.) and 10 μl of thiophosgene was added. After 15 minutes the hazy mixture was centrifuged, the yellow solid was washed with acetonitrile and centrifuged. The acetonitrile solution was stripped at reduced pressure to yield 3.1 mg of [Rh(BITC-2,3,2-tet)Cl$_2$]+; The aqueous phase of the mixture, after centrifugation, was loaded on to a Chrom-Prep column washed with saturated sodium chloride, then water and eluted with acetonitrile. The acetonitrile fraction was then concentrated at reduced pressure to yield 5.6 mg of the desired product, overall yield is 80%.

Example 3

Preparation of [$^{105}$Rh(BITC-2,3,2-tet)Cl$_2$]+

Ten μl of freshly made thiophosgene solution (10 μl of thiophosgene in 5 ml of 90% acetonitrile) was added to 400 μl of a solution of [$^{105}$Rh(BA-2,3,2-tet)Cl$_2$]+ in 90% acetonitrile. The solution was mixed immediately and then allowed to stand at room temperature (about 22° C.) for 20 minutes. The reaction mixture was then placed in a heating block (about 37° C.). Excess unreacted thiophosgene as well as the solvent were evaporated by a gentle jet of N$_2$ for one hour. The dry [$^{105}$Rh(BITC-2,3,2-tet)Cl$_2$]+, yield >95%, is free from any unreacted thiophosgene.

Example 4

Preparation of α-(4-isothiocyanatobenzyl)-1,4,7,10-tetraazacyclododecane-1,4,7,10-tetraacetic acid, samarium(III) complex A small sample, 7 mg, (10.8 μmole) of α-(4-aminobenzyl)-1,4,7,10-tetraazacyclododecane-1,4,7,10-tetraacetic acid, samarium(III) complex was dissolved in 400 μl water. Excess thiophosgene (50 μl) was added, followed by 400 μl CHCl$_3$ and the two-phase reaction stirred vigorously for 30 minutes. At the end of this time, the water layer was extracted with 500 μl CHCl$_3$, four times, and the water layer then was lyophilized to give the desired titled product in quantitative yield.

The UV showed this compound to have a band at 272 and 282 nm. The TLC, silica gel developed by 75:25 V:V CH$_3$CN:H$_2$O, gave $R_f$=0.38. The starting material has an $R_f$=0.19. The IR (KBr pellet) showed -SCN stretch at 2100 cm$^{-1}$; fast atom bombardment mass spectrum [M+H]+=687.

Example 5

Preparation of α-(4-isothiocyanatobenzyl)-1,4,7,10-tetraazacyclododecane-1,4,7,10-tetraacetic acid, sodium salt, yttrium(III) complex A small sample of the α-(4-aminobenzyl)-1,4,7,10-tetraazacyclododecane-1,4,7,10-tetraacetic acid, yttrium complex (10 mg, 17 μmole) was dissolved in 400 μl H$_2$O. To this solution was added 64 μl thiophosgene (500 μmole) and 400 μl CHCl$_3$ and the resulting mixture stirred vigorously for 40 minutes. During this time several small additions of solid NaHCO$_3$ were made to keep the pH at about 8. At the end of the reaction, the water layer was separated and extracted with 1 ml of CHCl$_3$, four times, and lyophilized. The title product was characterized by TLC and UV spectroscopy.

Example 6

Preparation of α-[2-(4-isothiocyanatophenyl)-ethyl]-1,4,7-10-tetraazacyclododecane-1,4,7,10-tetraacetic acid, samarium-153 complex To a solution of α-[2-(4-aminophenyl)-ethyl]-1,4,7,10-tetraazacyclododecane-1,4,7,10-tetraacetic acid, samarium-153 complex prepared from 150 μl of $^{153}$Sm solution in 0.1N HCl (about 4.6 mCi) was added 2 μl of HEPES buffer (0.5M, pH 8.9), 2 μl of thiophosgene and 200 μl of chloroform. The mixture was vortexed vigorously 2 or 3 times for a few seconds each time. The chloroform layer was discarded and the aqueous layer which contained mainly the desired product was saved and further purified. The yield of α-[2-(4-isothiocyanatophenyl)ethyl]-1,4,7-10-tetraazacyclododecane-1,4,7,10-tetraacetic acid, samarium-153 complex, based on $^{153}$Sm activity measurement by HPLC on GF-250 column using System I, was around 85-90 percent. To purify, the aqueous layer was passed through a Sep-Pak TM C-18 cartridge and eluted with 90% acetonitrile in water. The first 300 μl of effluent was discarded, and the SCN-derivative which came off in the next 900 μl was characterized by HPLC on GF-250. The recovery of the $^{153}$Sm activity was in general better than 90%. The bulk of the solvent was then evaporated off in a Speed Vac TM concentrator over a period of 1.5 to 2 hours.

Example 7

Preparation of α-(4-isothiocyanatophenyl)-1,4,7,10-tetraazacyclododecane-1,4,7,10-tetraacetic acid, samarium-153 complex To a solution of α-(4-aminophenyl)-1,4,7,10-tetraazacyclododecane-1,4,7,10-tetraacetic acid, samarium-153 complex prepared from 220 μl of $^{153}$Sm solution in 0.1N HCl were added 2 μl of HEPES buffer (0.5M, pH 8.9), 2 μl of thiophosgen and 200 μl of chloroform. It was vortexed vigorously 2 or 3 times for a few seconds each time. The chloroform layer was discarded and the aqueous layer which contained mainly the desired product was saved and further purified. The yield of α-(4-isothiocyanatophenyl)-1,4,7,10-tetraazacyclododecane-1,4,7,10-tetraacetic acid, samarium-153 complex, as analyzed by HPLC on GF-250 column based on the $^{153}$Sm activity using the HPLC System I was usually over 90%. To purify, the aqueous layer was passed through a Sep-Pak TM C-18 cartridge and eluted with 90 percent acetonitrile in water. The first 300 μl of effluent was discarded, and the desired product came off in the next 1200 μl, with 86-93% recovery. The bulk of the solvent was then evaporated off in a Speed Vac TM concentrator over a period of about 2 hours.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims:

What we claim is:

1. A process for preparing isothiocyanate compounds which comprises reacting thiophosgene with an amino functionalized polyaza chelate containing only primary and secondary amines complexed with rhodium.

2. The process of claim 1 wherein the polyaza chelant is 3-[(4-aminophenyl)-methyl]-1,5,8,12-tetraazacyclotetradecane.

3. The process of claim 1 wherein the polyaza chelant is 6-[(4-aminophenyl)methyl]-1,4,8,11-tetraazaundecane.

4. The process of claim 1 wherein the polyaza chelant is 1,4,7,10-tetraaza-1-[(4-aminophenyl)methyl]cyclododecane.

5. The process of claim 1 wherein the polyaza chelant is 6-(3-aminopropyl)-1,4,7,11-tetraazaundecane.

6. The process of claim 1 wherein a polar solvent or mixture of solvents is present.

7. The process of claim 6 wherein the mixture of solvents is water with a polar organic solvent selected from the group comprising ethanol, acetonitrile, dimethylformamide, tetrahydrofuran and dioxane.

8. The process of claim 6 wherein the polar solvent is selected from the group comprising water, ethanol, acetonitrile, dimethylformamide, tetrahydrofuran and dioxane.

9. The process of claim 1 wherein the pH of the reaction is from about 2 to about 10.

10. The process of claim 1 wherein the temperature is from about 0° to about 50° C.

11. The process of claim 10 wherein the temperature is room temperature.

12. The process of claim 1 for preparing [$^{105}$Rh(BITC-2,3,2-tet)Cl$_2$]+ which comprises reacting [$^{105}$Rh(BA-2,3,2-tet)Cl$_2$]+ with thiophosgene in water at room temperature.

13. The process of claim 1 for preparing [$^{105}$Rh(BITC-2,3,2-tet)Cl$_2$]+ which comprises reacting [$^{105}$Rh(BA-2,3,2-tet)Cl$_2$]+ with thiophosgene in water/acetonitrile at room temperature.

14. The process of claim 1 for preparing [$^{105}$Rh(BITC-2,3,2-tet)Cl$_2$]+ which comprises reacting [$^{105}$Rh(BA-2,3,2-tet)Cl$_2$]+ with thiophosgene in water/acetonitrile at room temperature and removing the solvents by evaporation and nitrogen stream.

* * * * *